(12) United States Patent
Metzger et al.

(10) Patent No.: US 9,168,342 B2
(45) Date of Patent: Oct. 27, 2015

(54) MEDICAMENT BLISTER

(75) Inventors: Burkhard Metzger, Ingelheim (DE); Johannes Geser, Ingelheim (DE); Hubert Hoelz, Oberheimbach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1786 days.

(21) Appl. No.: 11/996,822

(22) PCT Filed: Jul. 24, 2006

(86) PCT No.: PCT/EP2006/064581
§ 371 (c)(1), (2), (4) Date: Mar. 21, 2008

(87) PCT Pub. No.: WO2007/012628
PCT Pub. Date: Feb. 1, 2007

(65) Prior Publication Data
US 2008/0197045 A1    Aug. 21, 2008

(30) Foreign Application Priority Data
Jul. 27, 2005 (DE) .................. 10 2005 035 705

(51) Int. Cl.
| | |
|---|---|
| B65D 85/42 | (2006.01) |
| A61M 15/00 | (2006.01) |
| B29C 65/50 | (2006.01) |

(Continued)

(52) U.S. Cl.
CPC ....... *A61M 15/0048* (2014.02); *A61M 15/0045* (2013.01); *A61M 15/0051* (2014.02); *B29C 65/5057* (2013.01); *B29C 66/53461* (2013.01); *B65D 75/327* (2013.01); *B29C 65/02* (2013.01); *B29C 65/4815* (2013.01); *B29C 65/5021* (2013.01); *B29C 66/21* (2013.01); *B29C 66/24* (2013.01); *B29K 2023/06* (2013.01); *B29K 2023/12* (2013.01); *B29K 2027/06* (2013.01); *B29K 2027/08* (2013.01); *B29K 2027/12* (2013.01); *B29K 2067/00* (2013.01); *B29K 2069/00* (2013.01); *B29K 2077/00* (2013.01); *B29K 2305/02* (2013.01); *B29L 2009/003* (2013.01); *B29L 2031/7164* (2013.01)

(58) Field of Classification Search
USPC .................. 206/528, 529, 530, 531, 532, 538
See application file for complete search history.

(56) References Cited

U.S. PATENT DOCUMENTS

| | | | |
|---|---|---|---|
| 4,076,789 | A | 2/1978 | Geller et al. |
| 4,627,432 | A | 12/1986 | Newell et al. |

(Continued)

FOREIGN PATENT DOCUMENTS

| | | |
|---|---|---|
| CA | 1 224 992 | 8/1987 |
| CA | 2 037 421 C | 9/1991 |

(Continued)

OTHER PUBLICATIONS

International Search Report for PCT/EP2006/064581 mailed Mar. 22, 2007.

*Primary Examiner* — Jacob K Ackun
(74) *Attorney, Agent, or Firm* — Michael P. Morris; Alan R. Stempel

(57) ABSTRACT

The present invention relates to medicament blisters for powder inhalers. The blisters according to the invention contain an inhalable powder comprising a medicament. The blisters are characterized by a reduced permeability for water vapor, which is achieved by decreasing the height of the sealing lacquer layer.

19 Claims, 4 Drawing Sheets

(51) Int. Cl.
| | |
|---|---|
| *B65D 75/32* | (2006.01) |
| *B29C 65/02* | (2006.01) |
| *B29C 65/00* | (2006.01) |
| *B29K 23/00* | (2006.01) |
| *B29K 27/06* | (2006.01) |
| *B29K 27/00* | (2006.01) |
| *B29K 27/12* | (2006.01) |
| *B29K 67/00* | (2006.01) |
| *B29K 69/00* | (2006.01) |
| *B29K 77/00* | (2006.01) |
| *B29K 305/02* | (2006.01) |
| *B29L 9/00* | (2006.01) |
| *B29L 31/00* | (2006.01) |
| *B29C 65/48* | (2006.01) |

(56) References Cited

U.S. PATENT DOCUMENTS

| | | | | |
|---|---|---|---|---|
| 4,778,054 | A * | 10/1988 | Newell et al. | 206/531 |
| 5,089,321 | A * | 2/1992 | Chum et al. | 428/218 |
| 5,360,116 | A * | 11/1994 | Schmiletzky | 206/531 |
| 5,589,275 | A * | 12/1996 | Breitler et al. | 428/458 |
| 5,598,425 | A | 1/1997 | Jain | |
| 5,911,325 | A | 6/1999 | Breitler | |
| 6,698,425 | B1 * | 3/2004 | Widerstrom | 128/203.25 |
| 6,752,148 | B1 * | 6/2004 | McGinn et al. | 128/203.15 |
| 6,793,077 | B1 | 9/2004 | Kancsar | |
| 6,896,139 | B2 | 5/2005 | Kancsar | |
| 7,854,225 | B2 | 12/2010 | Pasbrig | |
| 2004/0104142 | A1 | 6/2004 | Dobler | |
| 2004/0173497 | A1 | 9/2004 | Kancsar | |
| 2005/0249903 | A1 * | 11/2005 | Kendig et al. | 428/35.7 |
| 2006/0102511 | A1 | 5/2006 | Pasbrig | |

FOREIGN PATENT DOCUMENTS

| | | |
|---|---|---|
| CA | 2 375 178 A1 | 12/2000 |
| DE | 33 36 486 A1 | 4/1984 |
| DE | 41 06 379 A1 | 9/1991 |
| DE | 33 48 370 C2 | 10/2001 |
| EP | 0 703 157 A1 | 3/1996 |
| EP | 0 905 042 A1 | 3/1999 |
| JP | 7257639 A | 10/1995 |
| JP | 8143032 A | 6/1996 |
| JP | 95212234 A | 12/1997 |
| JP | 2712254 B2 | 2/1998 |
| JP | 2000192260 A | 7/2000 |
| JP | 2003501321 A | 1/2003 |
| JP | 2003534051 A | 11/2003 |
| JP | 2006036310 A | 2/2006 |
| JP | 2006504591 A | 2/2006 |
| WO | 00/075037 A1 | 12/2002 |
| WO | 2004041672 A2 | 5/2004 |

* cited by examiner

MEDICAMENT BLISTER

The present invention relates to medicament blisters for powder inhalers. The blisters according to the invention contain an inhalable powder formulation including a medicament. The blisters are characterised by a reduced permeability to water vapour.

PRIOR ART

Medicinal aerosol therapy, in which an active constituent is absorbed by inhalation through the lungs, plays an important rôle in the treatment of many lung diseases. In order to administer the medicaments nebulisers, metering aerosols or dry powder inhalers are often used.

In the field of powder inhalers single dose appliances and multi-dose appliances are known. Particularly interesting are appliances in which individual doses of the medicament formulation are present in packaged units, especially in the form of blister packs.

The way and means in which the powder formulation is packaged in the appliance is decisive for the product quality and thus the suitability for inhalative uses.

DE 3348370 and DE 3336486 disclose inhalers that comprise a disc-shaped blister pack. The blisters consist of a floor film or floor sheet that comprises a plurality of circularly arranged cavities. The cavities may be open to one or two oppositely facing sides. The openings are accordingly all situated on the same front side or on both front sides. The individual cavities contain in each case a dose of a specified medicament powder for inhalation. The openings of the cavities are closed by a sealing film. The cavity is opened to release the medicament powder. An air channel connects the opened cavity to the mouthpiece of the inhaler. The inhaler of DE 3336486 is described in more detail by way of example. This inhaler comprises a housing in which is arranged a chamber (storage chamber) that comprises an air inlet and in which is arranged a disc-shaped, round blister with packaged medicament pockets. The blister is loosely connected via the front side or floor side to the front side of a round, rotatable disc. Holes are formed circumferentially on the disc so that the medicament pockets of the blister can be arranged over the holes of the rotating disc. The inhaler comprises a piston that is arranged so that it can in each case penetrate and open a medicament pocket, so that the medicament is released into a chamber and can be breathed in via an air channel through the mouthpiece by the user. Reference is made to the drawings of the patent application and to the US patent specification.

DE 4106379 describes an inhalation appliance in which a blister strip is incorporated that comprises a row of a plurality of linearly arranged cavities containing the pulverulent medicament formulation. The blister strip consists of two material strips that can be peeled apart. The blister strip comprises a base film that contains cavities, the openings of all cavities lying on the same side of the base film. The openings are closed by the sealing film lying thereabove. The appliance is provided with a device that peels the two material strips from one another at an opening station, in order to open a container. The user can inhale the pulverulent medicament from the opened container via an outlet part, for example a mouthpiece, that is connected to the opened container. A drive device that peels the carrier strip and the cover strip from one another may be provided at the opening station. This drive device consists for example of two drive wheels (e.g. toothed wheels), that hold the cover strip in drive engagement. In this case too each individual blister cavity defines a type of storage chamber in the inhaler that is connected via an air channel to the mouthpiece.

One of the tasks of the blisters is to protect the inhalation formulation against chemical or physical change. Physical changes include in this connection in particular changes that can affect the release of the predetermined finely particulate dose. The term finely particulate dose is understood in this connection to mean the dose that reaches the patient's lungs. This is influenced by the interactions of the micronised active constituent particles with one another as well as the interactions with the auxiliary substances. It has been found that, particularly due to the change in the degree of moisture in the interior of the packaging, these interactions can increase to such an extent that the fine particle dose is significantly reduced. Such changes include in this connection the penetration of water into the packaging, as well as the removal of water from the interior of the packaging.

Accordingly, one of the main tasks of the blister packaging is to maintain constant the chemical composition of the atmosphere in the interior of the packaging in order to avoid physical or chemical changes in the active constituent formulation, and to maintain stable the inhalation formulation. In this connection a distinction is made between a short-term stability, which the inhalation formulation per se must possess, even if it not sufficiently protected by the packaging means ("in use stability"), and the long-term stability, i.e. the stability that must be ensured so long as the inhalation formulation is contained in the unopened packaging means.

The packaging must therefore primarily ensure that the inhalation formulation remains stable over the long term. If the material and the structural configuration of the primary packaging means cannot guarantee this, then the secondary packaging means must do so. The choice of a suitable material for the primary packaging means is determined by two factors: on the one hand the material must be able to satisfy the discussed protective function. On the other hand the material must be such that the primary packaging can be given the necessary shape for use in the powder inhaler and that the primary packaging means can meet its intended function.

In order to reduce the water vapour permeability of the blisters, in the prior art attention is focussed in particular on the film materials of which the blisters are composed. Interesting blisters according to the invention include blisters with a floor film of plastics and/or aluminium and a sealing film of aluminium. In this connection the sealing film is bonded to the floor film via a sealing lacquer, which is applied to the whole surface of the sealing film.

It has now surprisingly been found that in the case of the aforedescribed blisters it is not only the film materials that are responsible for a permeation of water vapour from outside into the blister, but in an unexpected way the sealing lacquer layer, with which the sealing film is fixed to the floor film, makes a significant contribution. This result is all the more surprising since the height of the sealing lacquer layer is only a few microns and is thus hardly present on the surface of the blister.

DESCRIPTION OF THE INVENTION

The present invention relates to blisters for medicaments for single dose or multi-dose powder inhalers. Preferred are blisters in which a plurality of individual doses of the inhalation formulation are present packaged in a blister strip or a blister disc. The blisters are characterised in this connection by the height of the sealing lacquer layer, or in the case of a sealed blister, by the height of the outwardly visible surface of the sealing lacquer layer.

According to the invention it is of minor importance whether in the blisters the inhalation formulation is present directly packaged (the blister is the primary packaging), or whether the inhalation formulation is present packaged in a further container (the blister is a protective secondary packaging).

According to the invention blisters are preferred that are designed as primary packaging and are a constituent of a ready-for-use powder inhaler.

The feature "constituent" or "integral constituent of a usable or ready-for-use inhaler" means that the blister is an element in the inhaler without which the charging of the inhaler with the medicament formulation (inhalation formulation) is not possible or is not envisaged for the purposes of the inhalation. This element can in the ready-for-use state (usable state) be rigidly connected to the inhaler, so that it cannot be removed in a non-destructive manner or without damaging the inhaler, or is non-destructively loosely or detachably connected to the inhaler.

Usable means that blister according to the invention is present inserted into the inhaler.

The blisters according to the invention are particularly suitable for packaging water-sensitive inhalation powders.

The purpose of the blister packaging is to minimise the exchange of matter between the interior of the packaging and the surroundings.

A further object of the invention consists in packaging inhalation formulations with a water-sensitive medicament in a multi-dose powder inhaler with pre-dosed individual doses in such a way that the penetration of moisture into the formulation is delayed compared with containers known from the prior art.

Yet a further object consists in reducing the penetration of water vapour through the sealing lacquer layer compared to the systems known from the prior art.

DESCRIPTION OF THE INVENTION IN DETAIL

The present invention relates to blisters with individual blister pockets or cavities, or pockets or cavities arranged in rows, and in particular relates to blister strips or blister discs. The blisters consist of a floor film with cavities and at least one sealing film. The two films are joined to one another via a sealing lacquer layer. The sealing lacquer layer is generally applied in an area-covering manner to one of the two front sides of the sealing film. This side of the sealing film is then connected under heat and/or pressure in an area-covering manner to the side of the floor film on which the openings of the cavities are formed. If necessary the floor film is sealed on both sides in this way.

The configuration of the blister according to the invention is if necessary predetermined by the powder inhaler to be used.

According to the invention the blisters are therefore a composite film or a laminate of
 a) a base element with at least one cavity open to at least one side,
 b) at least one sealing film that is welded to the base element so that the at least one cavity is sealed with the formation of a hollow space with a medicament formulation embedded therein, and
 c) an intermediately arranged sealing lacquer layer that joins the base element and the sealing film to one another.

In the simplest case the blister therefore consists of three layers: the base element with the upwardly open cavity is at the bottom, above this is the sealing lacquer layer, and above the latter is the sealing film. Further layers may be formed on both sides of this laminate. The type of materials used and the number of layers influences the water vapour permeability from outside into the cavity and vice versa, as well as the mechanical stability of the blister.

Materials

The base element is formed from a metal film, polymer film, a metal body and/or polymer body. Aluminium or an aluminium film or an aluminium composite film of aluminium and for example a plastics is preferred as metal or metal film. As material for the plastics films there may be used PVC (polyvinyl chloride), COC (cycloolefin copolymer, e.g. Topas®), cycloolefin polymer (COP), polychlorotrifluoroethylene (e.g. ACLAR®), polyethylene (e.g. as high density polyethylene or low density polyethylene), polypropylene, poly(vinylidene chloride) (PVDC), polyethylene terephthalate, polycarbonates, polyesters, polyacrylates, polyamides or another plastics.

The base element is often a thermoforming sheet, in which the cavities are formed. Such thermoforming sheets are also termed trough sheets in the present context if troughs or cups for accommodating the pharmaceutical formulation are formed in the film.

Alternatively the base element may also be a strong plastics or metal disc or surface.

In a further modification the base element consists of a plastics or a plastics film, the base element being completely or partly lined with a metal film, e.g. embodiments in which at least the cavity (cavities) is/are completely lined with the metal film. The inner part of the wall is in this connection the part of the wall of the medicament pocket that may come into contact with the medicament formulation.

Preferably the base element consists of an aluminium film, which may if necessary have a plastics coating on the side facing towards the product (side containing the cavity). In this case the plastics coating is as thin as possible, and its height is preferably less than or equal to 50 µm, more preferably less than or equal to 40 µm and particularly preferably less than or equal to 30 µm.

The sealing film is a metal and/or polymer film. It may be fabricated from the same materials as the base element.

A hot lacquer may be used as sealing lacquer. Hot sealing lacquers based on a polyacrylate and/or polyethylene (e.g. high density and/or low density polyethylene) are suitable.

Materials with low permeation coefficients for water are preferred. With mixtures, according to the invention the proportion of the constituents with high permeation is reduced as far as possible. Mixtures of poly(methyl acrylate) and poly (ethyl acrylate) are often used. Preferred are sealing lacquers that contain a mixture of poly(methyl acrylate) and poly(ethyl acrylate) in which the proportion of poly(methyl acrylate) to poly(ethyl acrylate) is 50 to 100% wt. %.

Supplementary layers may consist of the materials mentioned above, or of paper.

A preferred blister consists of a base element of an aluminium film or aluminium composite film, and a sealing film of an aluminium film or aluminium composite film. The sealing lacquer layer according to the invention is then arranged therebetween.

Configuration of the Base Element

The base element constitutes a surface in which cavities are formed. The two sides of the surfaces are preferably flat, if one disregards the cavities.

In the case of a base element with a plurality of cavities, these are arranged in a row, in parallel, in a circular or spiral arrangement, or in a plurality of rows. In this connection the openings of the cavities are preferably provided on the same side of the base element.

In the case of a base element with a plurality of cavities with in each case two openings, the two openings are preferably formed opposite one another (en face).

Although the dimensions of the cavities are according to the invention of minor importance, they shall be discussed for the purposes of illustration.

In the case of the preferred blisters formed as primary packagings, the length of the cavity(ies) in the base element is up to 10 mm, the width is up to 10 mm and the height is up to 5 mm, preferably up to 3 mm. The dimensions of the cavities in the case of the blisters for powder inhalers are often less, for example 6.4 mm×3.7 mm×1.6 mm (length×width×height) or 4 mm×2.65 mm×0.9 mm.

In the case of secondary packagings the dimensions may on the other hand be larger: for example 40 mm×25 mm×15 mm (length×width×height).

Each opening of a cavity is surrounded by a substantially flat web (bridge) oriented perpendicularly with respect to the opening. This web has a width of at least 0.5 mm, preferably 1 mm, more preferably 2 mm and most particularly preferably 4 mm.

The active constituent formulation may be present directly in the cavities, or the cavity may additionally comprise a trough (cup) in which the active constituent formulation is present. If necessary the active constituent may also be present in packaged form, e.g. in capsules, in the cavities.

The base element and the finished blister may be configured as strips or discs. A strip may be seen in FIGS. 3 and 5a, while a disc may be seen in FIG. 7.

Fixing of the Sealing Film and Base Element

The sealing film is connected to the base element so that the opening of each cavity is completely closed, i.e. a closed sealing seam surrounds the opening of each cavity. For this purpose the two layers are welded or bonded together at least at the edge of the blister, and preferably also directly around the cavity. The sealing film is employed preferably everywhere where it contacts the base element through the hot lacquer layer firmly fixed to the base element (homogeneous distribution of the sealing lacquer). In the ideal case the sealing film bonds over its whole surface area to the base element with the exception of the regions of the sealing film that are situated above the openings of the cavities.

In order to join the sealing film to the base element, a sealing lacquer layer (joining layer) is preferably homogeneously applied, e.g. in the form of a hot sealing lacquer layer, to the sealing film or to the base element. The sealing film and the base element are then brought into contact with one another so that the joining layer is present between the two layers. Under the action of pressure and heat the joining layer then secures the two other layers to one another. At the same time the joining layer may melt. The surface structure of the sealing lacquer layer after the sealing procedure is determined inter alia also by the sealing tools. In this connection the layer thicknesses of the sealing lacquer layer between two adjacent points may vary. For example, the sealing lacquer layer may form in cross-section a punctiform network. Accordingly the term "layer thickness" in the context of the description of the present invention includes not only embodiments with a homogeneous layer thickness and material distribution, but also inhomogeneous layer thicknesses and material distributions, as are known from the prior art. The term layer thickness then expresses the corresponding average values. Sealing lacquer layers with a homogeneous distribution of the lacquer are preferred.

Blisters are preferred in which the opening of the cavity on a surface is sealed over a width of at least 0.5 mm, preferably 1 mm, more preferably 2 mm and most particularly preferably 4 mm, over the whole circumference of the opening.

With reference to FIGS. 2, 4, and 6 in order to reduce the water vapour permeability of the sealing lacquer layer, a blister is proposed in which the height, h of the sealing lacquer layer 10 (e.g., see FIG. 6) after the welding and/or bonding procedure is up to 5 µm. Particularly preferred are average heights of 1 to 4.5 µm, in particular 2 to 4.5 µm. Most particularly preferred are average heights of 2 to 4 µm. For the purposes of comparison, in an average blister the overall height, consisting of the height of the base element 14 and of the sealing film 12, is of the order of magnitude of 80 µm. The height is the dimension of the seam that is vertical to the plane of the base element and of the sealing film.

In order to achieve this average height in the finished blister, the amount of sealing lacquer before the sealing procedure may be up to 10 g/m$^2$. Amounts of 1 up to 7 g/m$^2$, particularly preferably 2 to 5.5 g/m$^2$, are preferred.

Instead of the absolute height of the sealing lacquer layer, the relative surface of the sealing lacquer layer may also be used by way of approximation as characteristic feature. The relative surface is the outwardly oriented surface of the sealing lacquer layer and thus the cross-sectional surface through which water vapour can penetrate the system. Stated another way, the surface area of the relative, outwardly oriented surface of the sealing lacquer layer is to be limited as compared to a surface area of an outwardly oriented surface of the seal of the blister. The relative surface is according to the invention up to 0.035% of the total surface of the blister. Preferably values are: up to 0.03%, more preferably up to 0.025%, still more preferably up to 0.02%, and most particularly preferably up to 0.015%.

The term "outwardly visible surface" should be understood as the outwardly oriented surface of the seam. This is the part of the surface of the seam that is in direct contact with the environment of the blister, i.e. air, water vapour, and is the permeation surface.

The term "relative surface" is defined as the product of the outwardly visible surface and the quotient of the edge length of the seam plane of the sealing lacquer layer and the actual length of the seam of the sealing lacquer layer, in each case referred to a blister unit from a medicament pocket.

The actual length of the seam of the sealing lacquer layer is the component of the outwardly visible surface parallel to the sealing film or to the base element.

The seam plane is an imaginary surface tensioned by the seam, that separates the sealing film from the base element. This imaginary seam plane should terminate with the sealing film. Its edges lie of course in this plane. With blisters in which individual medicament pockets are arranged side by side, the edge of the seam plane is not primarily defined by the termination of the sealing film, but by the imaginary, central boundary between the medicament pockets, i.e. cavities. If no further medicament pocket lies between the edge of the sealing film and the medicament pocket, then in this case the edge of the sealing film should be taken, or in principle is regarded as cut by an imaginary central boundary. By means of this procedure the seam plane is standardised with reference to each individual cavity (medicament pocket), or each blister is treated as if it had only one single medicament pocket. The same principle is used to determine the length of the seam of the sealing lacquer layer.

If one now imagines a square blister consisting of a square sealing film and a base element dimensionally accurately matched thereto, the following result is obtained: the length of the seam of the sealing lacquer layer is equal to four times the edge length of the square.

The edge length of the seam plane is likewise equal to four times the edge length of the square.

Thus, the relative outwardly visible surface of the sealing lacquer layer is identical to the absolute outwardly visible surface of the sealing lacquer layer.

If one now imagines the blister as a square blister whose base element and sealing film consist of the same film, which was first of all folded in the middle, then the two part elements have been collapsed or folded on top of one another, resulting in a square blister that has a sealing surface on three edge sides, while the fourth side is the folding side.

In this case the length of the seam of the sealing lacquer layer is equal to three times the edge length of the square, while the edge length of the seam plane is equal to four times the edge length of the square. Accordingly, the relative outwardly visible surface is calculated to be ⁴⁄₃ times the absolute surface.

With a blister formed of two square individual blisters that are connected to one another via an edge, the situation is analogous to the blister with three sealing edges described above.

The relative configuration of the surface means that the reference point for the surface is always understood to be the resultant surface for a blister with a medicament pocket in which the overall edge length of the seam plane is formed as a sealing surface.

In an alternative mode of description the invention can also be described by the water vapour permeation through the sealing lacquer layer. Ideally the permeation in a state of stationary equilibrium ("steady state") with an atmospheric humidity in the space in the cavity of ca. 16% and an atmospheric humidity in the external surroundings of the blister of 75% and at a temperature of 40° C. for a period of 6 months, is less than or equal to 320 µg/mm² sealing lacquer layer, preferably 60 to 280 µg/mm² sealing lacquer layer, more preferably 120 to 280 µg/mm² sealing lacquer layer, and more particularly preferably 120 to 250 µg/mm² sealing lacquer layer.

A steady state is understood to be the state in which the sealing lacquer layer is saturated with water/water vapour.

Particular Configurations and Embodiments

One embodiment of the blister according to the invention relates to a blister disc. This consists of a cylindrical disc or base plate that preferably has a height of up to 5 mm and a diameter of up to 15 cm. Wells or holes (cavities) are formed in the disc perpendicular to the plane of the disc. The wells or holes are preferably formed on the outer edge of the disc and may be closed by one or more sealing films. The inhalation formulation is contained in the wells or holes. The disc-shaped body consists in this connection of the material used according to the invention. Such a disc may for example be used in an inhaler according to DE 3348370 or DE 3336486. Such an inhaler has a housing accommodating the disc-shaped, round blister with packed medicament pockets. The inhaler includes inter alia a pin that is arranged so that in each case it can open a medicament pocket, in order that the medicament is released into the chamber and can be breathed in through a mouthpiece.

In another embodiment the container is a strip-shaped flexible blister with a row of several linearly arranged medicament pockets, as is described in DE 4106379. The blister consists of at least two material strips that can be peeled from one another, which define at least one container in which the medicament is contained.

The associated inhaler is provided with a device that peels the two material strips from one another at an opening station, in order to open the blister. The user can inhale the pulverulent medicament from the opened container through an outlet part, such as a mouthpiece, that is connected to the opened container. In this connection one of the material strips may also be a carrier strip with a plurality of pockets, the other material strip being a cover strip. Each pocket and the adjoining region of the cover strip then form a container. A drive device that peels the carrier strip and the cover strip from one another may be provided at the opening station. This drive device consists for example of two drive wheels (e.g. toothed wheels), which maintain the cover strip in drive engagement. In this case too each individual blister forms a type of storage chamber in the inhaler that is connected via an air channel to the mouthpiece.

In a particular and preferred modification of the blister according to the invention the outwardly oriented edges of the blister are folded over or crimped over, and optionally the folding edge is bonded or welded to the inwardly facing region of the blister. Preferably the folding edge is folded back completely to the base element or the sealing film. The folding edge may lie up to 4 mm, preferably up to 2 mm, and more particularly preferably up to 1 mm from the edge. The folding has a double effect: on the one hand the permeation path for water vapour is lengthened, since the distance between the cavity and edge can be lengthened, and on the other hand the folding edge per se constitutes a constriction and thus a further permeation barrier. The preferred distance between the edge of the cavity and the closest lying edge is at least 1 mm, preferably at least 2 mm, more particularly preferably at least 3 mm. As already mentioned, the said distance may if necessary be lengthened by folding.

Alternatively or in addition thereto the surface of each outer edge may additionally be covered with a further sealing film (perpendicular to the laminate layers). The further sealing film may be restricted to the outer edge, though it may overlap the uppermost layer and the lowermost layer of the blister, or in the case of a folding edge can cover the outer edge. The further sealing film may be of the same material as the first sealing film, for example an aluminium film.

In a preferred embodiment the base element consists of an aluminium film and the sealing film likewise consists of an aluminium film. The sealing lacquer layer is interposed therebetween.

In a further preferred embodiment the base element consists of an aluminium film that is covered with a plastics layer. Over this lies the sealing lacquer layer, and over the latter lies a sealing film of aluminium. In this or similar cases the plastics layer is likewise kept as thin as possible. The plastics layer is joined via an adhesive layer to the aluminium film of the base element, the adhesive layer ideally being thinner than the sealing lacquer layer, preferably less than half the thickness of the sealing lacquer layer, and is at least less than 2.5 µm. The plastics layer preferably has a thickness of less than or equal to 50 µm, more preferably less than or equal to 40 µm, and particularly preferably less than or equal to 30 µm. One of the plastics already mentioned in connection with the base element may be used as plastics, i.e. PVC (polyvinyl chloride), COC (cycloolefin copolymer, e.g. Topas®), cycloolefin polymer (COP), polychlorotrifluorethylene (e.g. ACLAR®), polyethylene (e.g. as high density polyethylene or low density polyethylene), polypropylene, poly(vinylidene chloride) (PVDC), polyethylene terephthalate, polycarbonates, polyesters, polyacrylates, polyamides or other plastics. PVC is preferred.

The layer structure of the particularly preferred aluminium composite blister is as follows: the outerlying layer of the floor film consists of polyamide, which for example is biaxially stretched. The following aluminium layer acts as a water vapour barrier, and is joined to the polyamide layer, for example via an adhesive/bonding agent. The aluminium that is used is an alloy that exhibits a good cold formability, for example the alloy AA 8021B. The plastics layer facing towards the product is bonded to the aluminium layer by means of an adhesive. The plastics layer of PVC has a thickness as described in the above paragraph. The cover film consists of an aluminium layer on which a layer of hot sealing lacquer is applied (for example a 4 to 9 μm thick layer). The layer may be applied by a roller application method. When the cover film is sealed under the action of heat and pressure onto the formed base film the hot sealing lacquer melts and bonds to the plastics layer of the floor film. In general a printing prelacquer is applied to the outside of the aluminium layer, on which product details, e.g. name, the manufacturer, variable dates, etc. can be printed. In order to protect this printing against abrasion, a protective lacquer may also be applied.

In a further embodiment each of the previously described embodiments can be developed further in such a way that at least the outermost seam is formed by two aluminium films and the sealing lacquer layer. Further layers, e.g. plastics layers, may be formed between these aluminium layers (enclosed layers). In this case however the dimensions (length and width) of the enclosed layers are maintained somewhat smaller than those of the two aforementioned aluminium layers. In this way it is ensured that the outer edge of the blister is formed by a web that is itself formed from the two aluminium films bonded together by the sealing lacquer layer, without one of the enclosed layers directly sealing off the outer edge. Also, a minimal surface for the permeation of water vapour is formed in this way. For example, a trough film of plastics can in this way be completely surrounded by a floor-side aluminium film and a cover-side aluminium film, so that the edge of the plastics trough too is surrounded by the aluminium films.

Preferred Medicament Formulations

Preferred classes of active constituents that are made available for an inhalation formulation that is present in the receptacle according to the invention for powder inhalers: anticholinergics, antimuscarinics, steroids, betamimetics, PDE-IV inhibitors, LTD4 antagonists and EGFR inhibitors. Particularly preferred are anticholinergics, especially tiotropium. The latter is most particularly preferably present in the form of tiotropium bromide monohydrate. One aspect of the invention therefore relates to the blister according to the invention containing tiotropium bromide monohydrate.

The inhalation powders used in the blisters according to the invention contain, apart from the active constituent, also preferably at least one auxiliary substance. This may consist of an auxiliary substance fraction that is homogeneous as regards the mean particle size of the auxiliary substance particles (for example 15-80 μm), or may optionally be a mixture of coarser auxiliary substance with a mean particle size of 15 to 80 μm, and a finer auxiliary substance with a mean particle size of 1 to 9 μm. If auxiliary substance mixtures of coarser and finer auxiliary substance fractions are employed, then the proportion of finer auxiliary substance to the overall amount of auxiliary substance is preferably 1 to 20%.

As physiologically compatible auxiliary substances there may for example be mentioned monosaccharides (e.g. glucose or arabinose), disaccharides (e.g. lactose, sucrose, maltose), oligosaccharides and polysaccharides (e.g. dextrans), polyalcohols (e.g. sorbitol, mannitol, xylitol), salts (e.g. sodium chloride, calcium carbonate) or mixtures of these auxiliary substances with one another. Preferably monosaccharides or disaccharides are used, the use of lactose or glucose, in particular but not exclusively in the form of their hydrates, being preferred. Within the context of the invention lactose is particularly preferably used, and lactose monohydrate is most particularly preferably used.

FIGURES

Typical blister variants are shown by way of example in FIGS. 1 to 4.

FIG. 1 shows an example of a blister pocket with the sealing seam dimensions that form the mean sealing seam length U for water vapour. The blister is shown in plan view. The outer length of the blister pocket L (from outer end to outer end) is for example 36.5 mm, the length of the cavity L is 28.5 mm, the outer width is 25.5 mm, and the width of the cavity is 17.5 mm. In other embodiments the blister cavity has a volume of 21 mm$^3$ for a surface area of 22.5 mm$^2$, i.e. the length of the blister L (from outer end to outer end) is ca. 13 mm, the length of the cavity 1 is 4 mm, the outer width is 7.5 mm, and the width of the cavity is 2.65 mm.

FIG. 2 shows the permeation path d and the permeation surface (outwardly oriented surface of the sealing lacquer layer) D.

FIG. 3 a typical blister (1) within the scope of the present invention with a plurality of cups/cavities (6) is shown in plan view.

FIG. 4 shows a blister in cross-section, only one cup (6) being shown. The blister consists of a sealing film (2) that lies over a thermoforming film with a plurality of cups (3) not joined to one another, for accommodating the pharmaceutical product, a lower trough layer (4) and the protective layer (5) underneath the trough layer (4).

The arrows A point to the cover layer (2) and are intended to show the diffusion path of moisture through the cover layer (2)

The arrows B point to the floor-side layer (3, 4, 5) and are intended to show the diffusion path of moisture through the floor layer.

The arrow C points to the connection part between the cover layer and the floor layer, and the path the moisture can take through this region of the blister.

FIG. 5 shows a variant consisting of a cover-side sealing film (7), a floor-side aluminium film (9) and a plastics film (8) lying therebetween, which is completely surrounded by the aluminium films (7) and (9). FIG. 5a is a plan view, the cover film (7) being exactly as large as the floor film (9) and lying thereover (not shown.). FIG. 5b shows the cross-section along the edge D, and FIG. 5c shows the cross-section along the edge E. The sealing lacquer layer is not shown.

Figure 1:
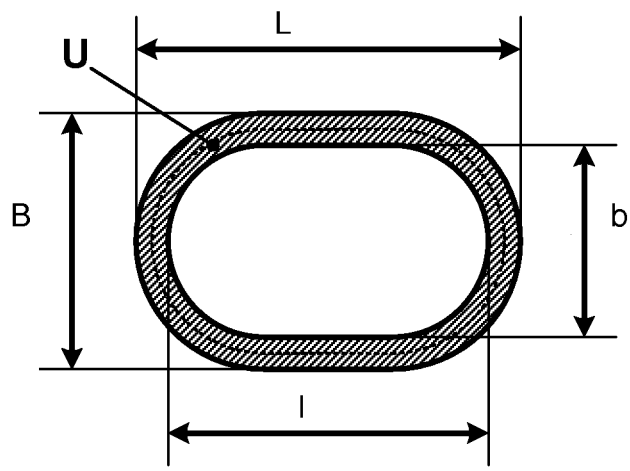
Figure 2:
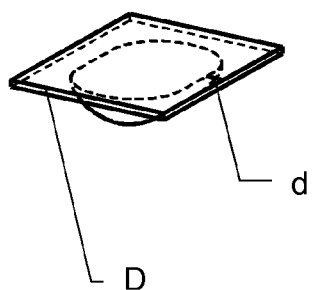
Figure 3:
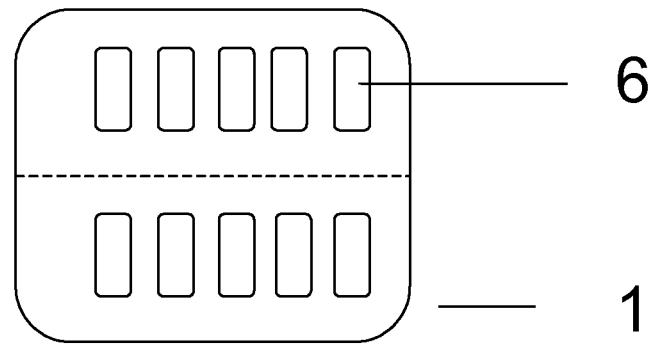
Figure 4:
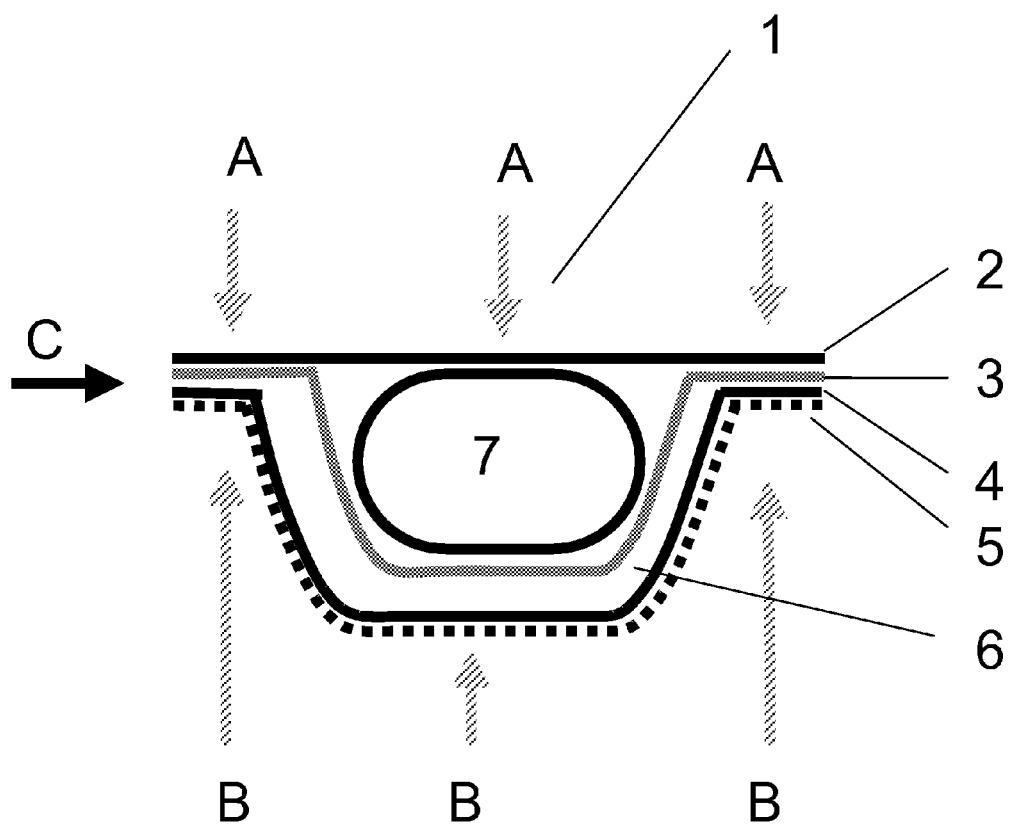
Figure 5A:
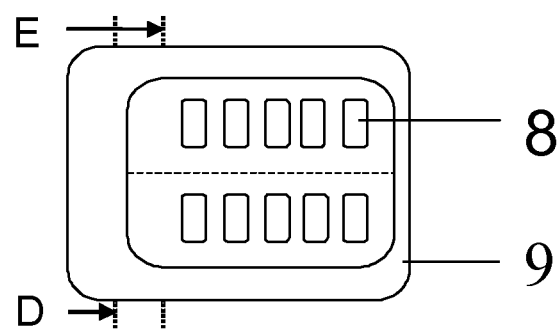
Figure 5B:
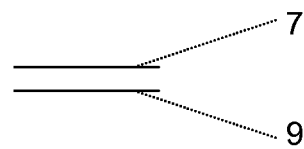
Figure 5C:
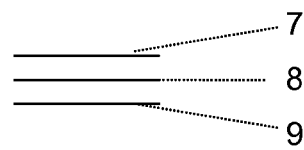
Figure 6:
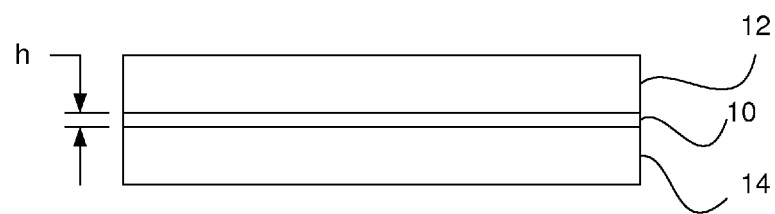
FIG. 6 shows a blister in which the height, h, of the sealing lacquer layer 10 after the welding and/or bonding procedure is up to 5 μm.
Figure 7:
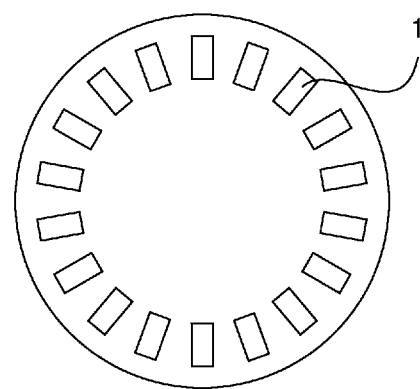
FIG. 7 shows a blister structure in the form of a disc.

Within the scope of the present invention blisters with the following layer sequence are preferred:

A sealing film consisting of a first layer (i.e. outermost layer) of paper (20 to 100 g/m$^2$) or lacquer (0.5 to 3 g/m$^2$), a second layer (2) situated thereunder, of polyethylene terephthalate, preferably in a thickness of 5 to 20 μm, more preferably 10 to 15 μm, and finally a layer of aluminium film in a preferred thickness of 10 to 60 μm, more preferably 10 to 50 μm and most particularly preferred 15 to 40 μm.

The base element for accommodating the pharmaceutical product (3) is arranged thereunder, which base element is formed for example from a three-layer film (4) in a preferred thickness of 30 to 500 μm, particularly preferably 60 to 300 μm. This film consists first of all of a PVC layer on the side touching the product, whose thickness is preferably 10 to 200 μm, particularly preferably 20 to 70 μm, and then of an aluminium layer whose thickness is preferably 30 to 60 μm, particularly preferably 35 to 50 μm. This aluminium layer is in turn covered by a layer of polyamide with a preferred thickness of 10 to 40 μm, particularly preferably 20 to 30 μm.

In this connection individual layers, for example the paper layer, may be omitted. The hot sealing lacquer layer according to the invention is for the sake of simplicity not considered here, but is nevertheless situated between the base element and the sealing film.

A further embodiment of a blister has the following layer sequence (from the top downwards): protective lacquer, printing ink, protective lacquer, 38 μm sealing film (aluminium film), hot sealing lacquer layer, 30 μm floor layer with cavity (PVC film), adhesive layer, 45 μm aluminium film, adhesive, adhesive layer, 25 μm film of oPA (oriented polyamide).

A further embodiment is a blister formed of three films. First, a cover film of a 38 μm thick cover layer of aluminium, then a 250 μm thick trough film of PVC for accommodating the pharmaceutical product, and finally a film lying thereunder, consisting of an aluminium layer in a thickness of 45 μm, and a floor-side occluding layer of polyamide in a thickness of 25 μm. The sealing lacquer layer according to the invention lies between the base element (in this case the trough film) and the sealing film of aluminium lying thereover.

The invention claimed is:

1. A blister for accommodating one or more individual doses of a medicament formulation, in which each individual dose is present in a completely closed cavity, containing
    a base element with at least one cavity open to at least one side,
    a sealing film that closes the at least one opening of the at least one cavity to form a hollow space with the medicament formulation embedded therein, and
    a sealing lacquer layer lying between the base element and sealing film,
    wherein a surface area of a relative, outwardly oriented surface of the sealing lacquer layer accounts for up to 0.035% of a surface area of an outwardly oriented surface of a seam including the base element, the sealing film, and the sealing lacquer layer of the closed blister.

2. The blister according to claim 1, wherein the cavity has a length of up to 10 mm, and a width of up to 10 mm.

3. The blister according to claim 1, wherein the opening of the cavity is sealed on a surface of at least 0.5 mm width over the whole circumference of the opening.

4. The blister according to claim 1, wherein the base element is an aluminium film and the sealing film is an aluminium film.

5. The blister according to claim 1, wherein the sealing lacquer layer is a polyacrylate and/or a polyethylene.

6. The blister according to claim 1, wherein the amount of applied sealing lacquer before the sealing procedure is up to 10 g per square meter, preferably 1 to 7 g per square meter, particularly preferably 2 to 5.5 g per square meter.

7. The blister according to claim 1, wherein outwardly oriented edges of the blister are folded.

8. The blister according to claim 1, wherein outwardly oriented edges of the blister are sealed with a film.

9. The blister according to claim 1, wherein the blister is a single cavity for accommodating a single individual dose, a single cavity for accommodating a plurality of separately packed individual doses, a strip with at least one row of linearly arranged cavities, or a blister disc.

10. The blister according to claim 1, wherein:
    the blister has a layer sequence of aluminium, plastics, aluminium, wherein the plastics is selected from the group PVC, COC, COP, polychlorotrifluorethylene, polyethylene, polypropylene, PVDC, polyethylene terephthalate, polycarbonate, polyester, polyacrylate, polyamide, preferably PVC, and
    a height of the plastics is equal to or less than one of: (i) 50 μm, (ii) 40 μm, and (iii) 30 μm.

11. The blister according to claim 1, wherein the surface area of the relative, outwardly oriented surface of the sealing lacquer layer accounts for up to 0.03% of the surface area of the outwardly oriented surface of the seam of the closed blister.

12. The blister according to claim 1, wherein the surface area of the relative, outwardly oriented surface of the sealing lacquer layer accounts for up to 0.025% of the surface area of the outwardly oriented surface of the seam of the closed blister.

13. The blister according to claim 1, wherein the surface area of the relative, outwardly oriented surface of the sealing lacquer layer accounts for up to 0.02% of the surface area of the outwardly oriented surface of the seam of the closed blister.

14. The blister according to claim 1, wherein the surface area of the relative, outwardly oriented surface of the sealing lacquer layer accounts for up to 0.015% of the surface area of the outwardly oriented surface of the seam of the closed blister.

15. A blister for accommodating one or more individual doses of a medicament formulation, in which each individual dose is present in a completely closed cavity, containing
    a base element with at least one cavity open to at least one side,
    a sealing film that closes the at least one opening of the at least one cavity to form a hollow space with the medicament formulation embedded therein, and
    a sealing lacquer layer lying between the base element and the sealing film,
    wherein a water vapour permeability through the sealing lacquer layer in a stationary equilibrium state is less than or equal to 320 μg/mm$^2$, measured at a relative atmospheric humidity in the cavity of 16% and an atmospheric humidity of external surroundings of the blister of 75%, at a temperature of 40° C., and over a period of 6 months.

16. The blister according to claim 15, wherein the water vapour permeability through the sealing lacquer layer in the stationary equilibrium state is from 60 to 280 μg/mm$^{2-}$.

17. The blister according to claim 15, wherein the water vapour permeability through the sealing lacquer layer in the stationary equilibrium state is from 120 to 280 μg/mm$^{2-}$.

18. The blister according to claim 15, wherein the water vapour permeability through the sealing lacquer layer in the stationary equilibrium state is from 120 to 250 μg/mm$^{2-}$.

19. The blister according to claim 1, wherein the base element and the sealing film are formed from aluminium and are joined at an outer edge of the blister by the sealing lacquer layer without any further plastic layers between the base element and the sealing film at the outer edge.

\* \* \* \* \*